(12) United States Patent
Kuhn

(10) Patent No.: US 7,074,041 B2
(45) Date of Patent: Jul. 11, 2006

(54) MEDICAL OR DENTAL-MEDICAL HANDPIECE HAVING A PUSH BUTTON FOR THE RELEASE OF A TOOL

(75) Inventor: Bernhard Kuhn, Biberach (DE)

(73) Assignee: Kaltenbach & Voight GmbH, Biberach (DE)

( * ) Notice: Subject to any disclaimer, the term of this patent is extended or adjusted under 35 U.S.C. 154(b) by 384 days.

(21) Appl. No.: 10/610,744

(22) Filed: Jul. 1, 2003

(65) Prior Publication Data

US 2004/0014005 A1    Jan. 22, 2004

(30) Foreign Application Priority Data

Jul. 2, 2002    (DE) ................. 102 29 649

(51) Int. Cl.
*A61C 1/14* (2006.01)
(52) U.S. Cl. ...................................... 433/127
(58) Field of Classification Search .............. 433/127, 433/128, 129, 126, 130; 279/155
See application file for complete search history.

(56) References Cited

U.S. PATENT DOCUMENTS

| 4,573,918 A | 3/1986 | Bareth ........................ 433/127 |
| 4,773,856 A * | 9/1988 | Mosimann ................... 433/127 |
| 4,781,589 A * | 11/1988 | Bareth ......................... 433/127 |
| 5,730,596 A * | 3/1998 | Rosenstatter ................. 433/127 |
| 5,836,766 A | 11/1998 | Gugel et al. ................. 433/127 |
| 2005/0158689 A1* | 7/2005 | Pernot ......................... 433/126 |

FOREIGN PATENT DOCUMENTS

| DE | 1 092 607 | 11/1960 |
| DE | 29 05 484 | 8/1979 |
| DE | 33 46 248 A1 | 7/1985 |
| EP | 374 276 | 6/1990 |
| EP | 820 734 A1 | 1/1998 |

* cited by examiner

*Primary Examiner*—Todd E. Manahan
(74) *Attorney, Agent, or Firm*—Marshall, Gerstein & Borun LLP

(57) ABSTRACT

A medical or dental-medical handpiece has in its forward end region a lateral insertion opening for a tool and, lying opposite to the insertion opening, a mounting opening with an insert part, which can he placed therein, and a push button which is mounted displaceably between an outer initial position and an inner release position and is biased into its initial position by a spring force. The pushbutton is supported with at least one stop arranged thereon on at least one counter stop in its intial position. The insert part is arranged sunk into the mounting opening and the pushbutton engages in the mounting opening with slight play for movement.

11 Claims, 2 Drawing Sheets

MEDICAL OR DENTAL-MEDICAL HANDPIECE HAVING A PUSH BUTTON FOR THE RELEASE OF A TOOL

BACKGROUND OF THE INVENTION

1. Field of the Invention

The invention relates to a medical or dental-medical handpiece.

2. Description of Related Technology

A handpiece is described for example in DE-AS 1 092 607. In the case of this known handpiece a holder device for a tool arranged in the forward end region of the handpiece has a drive sleeve which is arranged transversely to the longitudinal middle axis of the drive sleeve and is rotatably mounted in a rotary bearing having two roller bearings with a spacing from one another. The drive sleeve forms an insertion hole with a lateral insertion opening for the tool. On the side away from the insertion opening there is arranged a push button which can be pushed in against an elastic return force by means of finger pressure and thereby brings about a release of the tool. The push button has the cross-sectional form of a hat, with an outwardly outstanding flange at the lower edge of the hat shape, which flange engages behind an undercut in a screw part screwed into the handpiece and is thereby held on the handpiece in a manner such that it cannot be lost. The screw part serves on the one hand for an axial restriction of the rotary bearing and on the other hand the guiding and holding of the push button. With this known configuration there is present between the screw part and the handpiece a screw joint which runs out outwardly, which not only detracts from the appearance of the handpiece but in which also dirt and infection agents can collect. Further, for screwing in and screwing out of the screw part there is needed an engagement element on the screw part which is effective in a form-fitting manner, which is accessible from the outside and thus constitutes a further element in which dirt and infection agents can collect. Further the appearance of the handpiece is also diminished through such an engagement element.

In the case of a handpiece of modern construction, the screw part is formed with a flange lying upon the edge of the mounting opening, which serves the guiding and holding of a push button, which engages behind an undercut in the flange in the above-described manner. With this configuration there is likewise present between the flange in the handpiece a screw joint, whereby beyond this the flange bearing on the housing leads to an enlarged structure, which with regard to restricted treatment sites, in particular in the mouth of a patient, should be avoided.

SUMMARY OF THE INVENTION

The object of the invention is, with a handpiece of the kind indicated in the introduction, to reduce the susceptibility to contamination.

With the configuration in accordance with the invention, the screw part is arranged, at least in the region of its body part having the thread, sunk into the mounting opening, whereby the push button engages into the mounting opening with slight guide play. With the configuration in accordance with the invention there is thus present only the necessary joint for the movement of the push button. The joint between the handpiece and the insert part is arranged covered over, and thus not accessible for contamination from the outside. This applies also to an engagement element for the screwing in and screwing out of an insert part in the form of a screw part, which is likewise arranged covered over and thus not accessible for dirt and infection agents. The appearance of the handpiece is also improved. Since the insert part is arranged sunk in in the mounting opening, the configuration in accordance with the invention can also lead to a reduction of size of the structure.

Preferred features contribute to simple, economically manufacturable and small or space-efficient manners of construction. Further developments of the invention also lead to features which make possible a simple and rapid mounting of the push button.

BRIEF DESCRIPTION OF THE DRAWINGS

Below, advantageous configurations of the invention will be described in more detail with reference to the drawings. There is shown.

DETAILED DESCRIPTION

Figure 1:
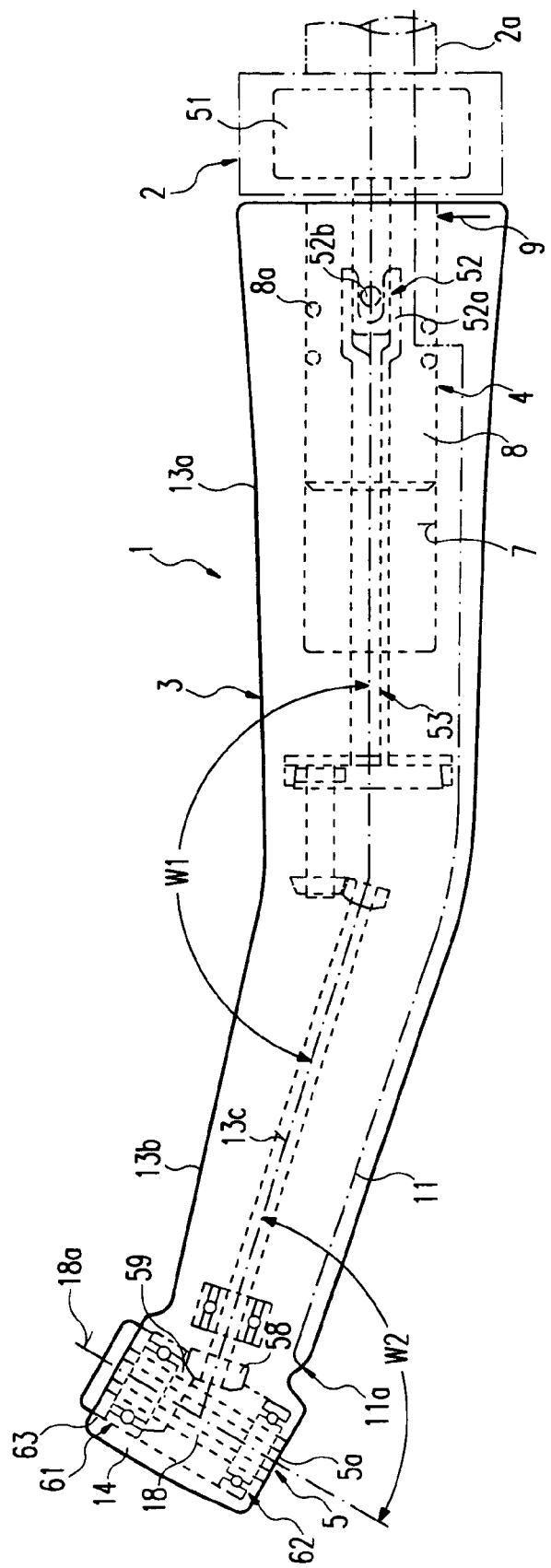
FIG. 1 a hand instrument for the treatment of the human or animal body having a handpiece in accordance with the invention, in a side view.

The treatment instrument, designated in its entirety by 1 in FIG. 1, consists of a rearward instrument part, namely a so-called connection part 2, and a forward instrument part, namely a so-called handpiece 3, which are releasably connected with one another by means of a coupling 4, in particular a plug-in coupling, preferably a plug-in/turn coupling. In the case of the present exemplary embodiment there is arranged at the forward end of the treatment instrument 1 a holder device 5 having a lateral insertion opening 5*a* for a tool, whereby the tool stands out to the side. The elongate handpiece 3 in the form of a shaft can extend straight (not shown) or curved towards the side away from the tool (not shown) or with an angle-shape with two shaft sections 13*a*, 13*b* including an obtuse angle. The plug-in/turn coupling is formed by means of a coupling recess 7, round in cross-section, and a coupling pin 8 which can be inserted therein with slight play for movement. In the case of the present exemplary embodiment, the coupling recess 7 is arranged at the rearward end of the handpiece 3, and the substantially cylindrical coupling pin 8 extends from the connection part 2 forwardly. In the coupled condition, the coupling recess 7 and the coupling pin 8 are releasably latched with one another by means of a latching device. This has a latching element 9 which is radially movably mounted in the one coupling part and biased by means of a spring force into a latching position passing through the dividing joint, in which position the latching element 9 engages into a ring groove in the other coupling part. Such a latching device latches self-actingly upon coupling, and upon de-coupling it can be overcome by means of manual exercise of an axial pulling force, whereby the latching element 9 is self-actingly displaced into its release position.

The connection part 2 is connected with a flexible supply line 2*a*, which is connected with a non-illustrated control apparatus. The handpiece 3 is freely rotatably mounted on the coupling pin 8, whereby handling is improved. Through the plug-in/turn coupling 4 there extends at least one media line 11 for a treatment or drive medium, e.g. water, compressed air or a water/air mixture (spray). The media line 11 extends Z-shaped through a hollow cylindrical dividing joint between the coupling recess 7 and the coupling pin 8, whereby the media line 11 passes through the dividing joint in the region of a ring groove in the coupling pin 8 or in the coupling recess 7, so that in any rotary position the passage of media is ensured. To both sides of the passage through the dividing joint this is sealed off by means of a sealing ring 8a, which may be arranged in a ring groove in the wall of the coupling recess 7 or in the outer surface of the coupling pin 8. Through this, a free rotatability through $360_E$ and more is ensured. The media line 11 extends from the rearward end of the treatment instrument 1 to its forward end region, whereby it may run in part as a channel in the instrument body or as a tube or pipe line. The media line 11 opens out in the forward end region of the treatment instrument 1, out of this, whereby the mouth opening 11a is directed at the treatment site or at the tip of the tool.

At the forward end of the handpiece 3 there is located a thickened head 14 in which a receiving sleeve 18 is mounted rotatably around a transversely running axis of rotation 18a, which sleeve forms at one side the insertion opening 5a and into which the tool can be inserted with its shaft and is releasably fixable by means of a fixing device in per se known manner.

The angle W2 enclosed in FIG. 1 between the middle axis 13c of the forward shaft section 13b and the axis of rotation 18a of the receiving sleeve 18 is preferably more than $90_E$, in particular substantially $100_E$. Such a configuration is, taking into account the anatomy of the mouth of a patient, particularly favourable.

A drive motor 51, e.g. an electric motor, is arranged in the connection part 2 illustrated by chain lines and is drivingly connected with the receiving sleeve 18 by means of a drive shaft or a drive shaft chain 53 having one or more drive shaft sections, rotatably mounted in the shaft of the handpiece. In the region of the plug-in coupling 4 the drive shaft 53 has a plug-in coupling 52 having two plug-in coupling elements 52a, 52b corresponding to one another in a form-fitting manner, through which upon coupling and de-coupling of the plug-in coupling 4 at the same time a coupling and de-coupling of the plug-in coupling 52 is possible.

The drive connection between the drive shaft 53 and the receiving sleeve 18 is formed by means of a gear transmission or an angled gear transmission having a gear 58 or conical gear on the forward end of the drive shaft 53 and a gear 59 or a conical gear on the receiving sleeve 18. The gear teeth engagement between the gears 58 and 59 is, with regard to the drive shaft 53, arranged on its side away from the tool. The receiving sleeve 18 can be rotatably mounted in the head 14 by means of two roller bearings 61, 62, which bearings have a spacing from one another directed along the axis of rotation 18a which is greater than the gear 58, so that the latter can be arranged with the gear 59 therebetween, including the gear 59, which is arranged on the side of the gear 58 away from the tool opening 5a and at the same time is arranged on the side of the roller bearing 61 towards the tool opening 5a, which is arranged further distant from the tool opening 5a than the other roller bearing 62. The bearing arrangement having the roller bearings 61, 62 can be mounted or demounted through a mounting opening 63 which is arranged in the head 14 on its side away from the tool opening 5a.

Figure 2:
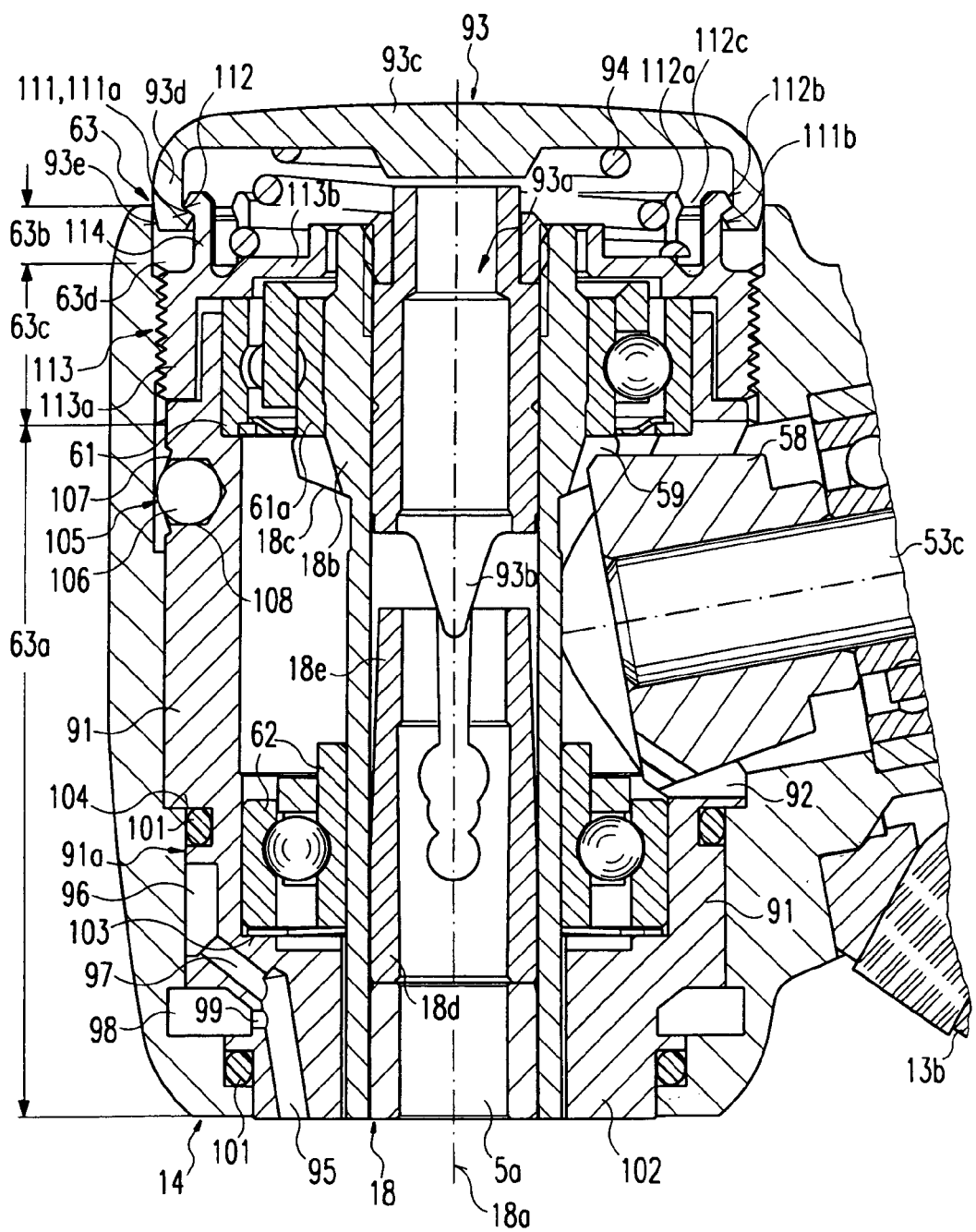
FIG. 2 the forward region of the handpiece in accordance with FIG. 1, in vertical longitudinal section.

As FIG. 2 by way of example shows, the receiving sleeve 18 may be mounted in the head 14 in a bearing sleeve 91 which is placed, fixed against rotation, in the mounting opening 63. The mounting opening 63 has in its forward region a fitting 91a, which if appropriate may be convergently stepped, in which the bearing sleeve 91 for the roller bearings 61, 62 sits. The free end region of the mounting opening 63 is formed as a cylindrical guide section 63b. Therebetween there is arranged a screw section 63c having an inner thread, the diameter of which is the same as or smaller than the diameter of the guide section 63b, as FIG. 2 shows.

In the case of the exemplary embodiment illustrated in FIG. 2, the outer rings of the roller bearings 61, 62 each sit in a fitting in the bearing sleeve 91, whereby they may bear on a shoulder surface which is away from the tool opening 5a.

It is possible, and advantageous for reasons of simple construction and good running properties, to form the bearing sleeve 91 as a common outer ring for both roller bearings, so that a double-rowed roller bearing is provided. With such a configuration, the outer rings of the roller bearings are omitted, the associated running races being arranged in the inner surface of the bearing sleeve 91.

With all above-described configurations it is possible and advantageous when the bearing sleeve 91 extends in substance up to the side of the head 14 containing the insertion opening 5a and there is arranged in the end region of the bearing sleeve 91 towards this side at least one delivery channel section 95 for a treatment medium, e.g. compressed air and/or water and/or at water/air mixture (spray), the opening out of which is directed in the direction towards the treatment site or towards the tool. For the connection of the convergent supply line section 95 with the media line 11, which in the case of the exemplary embodiment according to FIG. 2 does not open out at 11a, there may be arranged a ring channel 96 in the outer surface of the bearing sleeve 91, which extends over the entire periphery or only over a part of the periphery and into the rearward region of which the media line 11 opens. The ring channel 96 may be connected by means of an obliquely running connection channel 97 with the supply line section 95.

In the case of the presence of two media lines 11 for two different treatment media, e.g. air and water, there may be provided a second ring channel 98, arranged axially offset, which is connected likewise with the supply line section 95 by means of a transversely running connection channel 99. To both sides of the ring channel or channels 96, 98, the bearing sleeve 91 is sealed in each case in the fitting 91a or receiving bore by means of a sealing ring 101 which sits in a ring groove in the outer surface of the guide sleeve 91 or in the inner surface of the fitting 91a and cooperates sealingly with the respective opposing wall.

There may be a plurality of supply channel sections 95 arranged distributed around the periphery, which in each case are connected with the associated ring channel or channels 96, 98.

The case of the exemplary embodiment, the bearing sleeve 91 is radially thickened in the region in which the at least one delivery line section 95 is arranged, whereby it may extend radially inwardly up to the drive sleeve 18 whilst maintaining a play for movement. Through this thickening 102 an inner shoulder 103 can be formed on which the roller bearing 62 bears, here with its outer ring.

For axial restriction of the bearing sleeve 91 towards the insertion opening 5a, the fitting 91a or the receiving hole has at least one inner shoulder 104 on which the bearing sleeve 91 bears with an outer shoulder, preferably in an axial position in which the insertion opening 5a ends flush with the associated side of the head 14.

The bearing sleeve 91 is secured against rotation by means of a rotation lock 105. For this purpose it has locking projections 106 standing out from its surface, which engage into an axial locking groove 107 in the inner surface of the receiving hole, whereby the groove 107 runs out towards the side away from the insertion opening 5a. The locking projection 106 is preferably formed by means of a ball which comes into place or arrests in a hole 108, e.g. through jamming.

The forward drive shaft section 53c with its forward gear 58 engages through the bearing sleeve 91 in a radial through guide hole 92, and it meshes with the gear 59 arranged between the inner bearing rings and partially within the bearing sleeve 91. The latter gear is with regard to the gear 58 preferably arranged offset towards the side away from the insertion opening 5a, so that it engages with the gear 58 on its side away from the insertion opening 5a. In the case of the exemplary embodiment, the gear 59 is arranged on an end thickening 18b of the receiving sleeve 18, e.g. formed in one piece. On the thickening 18b, formed externally cylindrically at least in sections, the inner bearing ring 61b of the associated roller bearing row can be mounted and preferably bear on a flange 18c of the thickening 18b with its end towards the insertion opening 5a, on which flange also the teeth on the side away from the inner bearing ring 61b may also be formed. Between the axis of rotation 18a in the middle axis 13c there is enclosed the angle W2.

There may be arranged in the receiving sleeve 18, in its region towards the insertion opening 5a, a per se known clamping sleeve 18d, having clamping jaws 18e opposite one another, for the shaft of the tool 5. For releasing the tool 5 there is arranged on the side away from the insertion opening 5a a release device 93, having a release pin 93a which is axially displaceably mounted in the receiving sleeve 18 and for releasing the tool is displaceable between the clamping jaws 18e with a wedge 93b. For actuation of the release pin 93a there is provided a push button 93c which by means of finger pressure is displaceable against the force of a compression spring 94 arranged covered over by a cover wall of the push button 93c, from an initial position illustrated in FIG. 2 into a non-illustrated release position retracted into the head 14. The return of the release pin 93 and of the push button 93c is effected self-actingly by means of the spring force.

The outer size of the push button 93c is adapted to the cross-sectional size of the guide section 63b with a slight movement or guide play. The cross-sectional shape of the push button 93c is hat-like, with a cover wall and the ring wall 93d standing up from this in direction towards the head 14. In the initial position, the ring wall 93d engages at least slightly into the guide section 63b. For simplification of the introduction upon mounting, the ring wall 93d may have in its free outer edge a rounded or oblique lead-in surface 93e which in the initial position of the push button 93c is located within the guide section 63b, so that the ring gap between the ring wall 93d and the inner surface of the guide section 63b is restricted to the guide play.

The outwards movement of the push button 93c is restricted by means of one or more stops 111, arranged distributed around a periphery of the push button 93c, which cooperate in a form-fitting manner with one or more counter stops 112 arrranged distributed around the periphery and engage behind the counter stop or stops 112. The counter stop or stops 112 are arranged on an insert ring 113 which is arranged so far sunk into the mounting opening 63 that the guide section 63b surrounds a ring free space 63d. In the case of the exemplary embodiment, the insert ring 113 is a screw ring having an external thread which is screwed into the screw section 63c. The insert ring 113 can be formed angle shaped in cross-section with a peripheral wall 113a and a radially inwardly extending flange wall 113b. For reducing the axial length, the peripheral wall 113a may engage into a corresponding ring recess at the relevant end of the bearing sleeve 91, so that the peripheral wall 113b surrounds the associated roller bearing 61, e.g. with radial spacing. Through this, the flange wall 113b can axially restrict the bearing sleeve 91 and/or the roller bearing 61 on the side away from the insertion opening 5a.

The stops 111 or the counter stops 112 are so elastically yielding that the thus constituted stop device axially positions the push button against the force of the spring 94 up to a certain size of the spring force. When the spring force exceeds a certain value the elastically yielding stop parts give way, so that the stop device can be overcome. This applies both for an outwardly directed axial movement and also for an inwardly directed axial movement of the push button 93c. Through this, the mounting or de-mounting of the push button 93c is ensured. For mounting, the push button 93c is pushed with its stops 111 over the counter stops 112, whereby the elastically yielding stop parts deflect and in the initial position of the push button 93c spring back, through which the engagement behind is ensured.

In the case of the exemplary embodiment there is provided a ring stop 111 as a ring beading 111a on the inner peripheral wall of the ring wall 93d. The counter stops 112 are arranged on in substance axially extending spring arms 114 which extend from the insert ring 113, in particular from its flange wall 113b, towards the side away from the insertion opening 5a, and at their free end regions have the outwardly projecting counter stops 112 in the form of ring beading segments 112a.

In order to ensure the above-described overcoming of the stop device at least for an inwardly directed mounting movement, and preferably also for an outwardly directed demounting movement, the stop or stops 111 and/or the counter stops 112 have lead-in surfaces 111b, 112b formed by means of oblique or rounded flanks, which ensure the elastic deflection or bending out of the elastically yielding stop parts.

The compression spring 94 is arranged within the spring arms 114, whereby the spring arms 114 can form a centring arrangement for the compression spring 94. As FIG. 2 shows, the walls of the compression spring 94, due to their convergent or divergent form, can be pressed together into a position in which there at least partially arranged next to one another, through which the compression spring 94 requires a lesser axial space.

The main parts of the head 14 of the handpiece 3, namely the drive sleeve 18, the bearing sleeve 91, the peripheral wall 14a of the head, the push button 93c and the insert ring 113 are preferably of corrosion resistant steel.

The insert ring 113 has externally accessible engagement elements with which a rotary tool can cooperate for the screwing or screwing out of the insert ring 113. In the case of the exemplary embodiments, the engagement elements can be formed by means of the gaps 112c arranged between the ring segments.

The invention claimed is:

1. Medical or dental-medical handpiece comprising a forward end region defining a lateral insertion opening for a tool and, lying opposite to the insertion opening, a mounting opening having a free edge region with an insert part, which can be placed therein, and a push button displaceably mounted between an outer initial position and an inner release position and biased into its initial position by a spring force, in which initial position the push button is supported with at least one stop arranged thereon one at least one counter stop, wherein the insert part is disposed sufficiently far into the mounting opening that there remains in the free edge region of the mounting opening a hollow cylindrical guide section, and the push button is adapted to the cross-sectional size of the guide section with slight play for movement and engages therein;

wherein the stop is arranged on the inside of an inwardly extending ring wall of the push button.

2. Handpiece according to claim 1,
wherein at least one of
the stop and the counter stop is elastically yielding transversely of the displacement direction of the push button so that when the push button is pushed in or pushed out with a pushing force exceeding the necessary stop force, the stop or counter stop elastically deflects and self-actingly springs back into the initial position.

3. Handpiece according to claim 1,
wherein
the stop is formed by means of ring beading on a ring wall defined in the push button.

4. Handpiece according to claim 3,
wherein
a plurality of counter stops are distributed segment-like on the periphery of the ring wall.

5. Handpiece according to claim 4,
wherein
the counter stops are arranged on a plurality of spring arms distributed on the periphery of the ring wall, which spring arms stand up from the insert part approximately axially towards the side away from the insertion opening.

6. Handpiece according to claim 5,
wherein
the spring arms extend approximately axis-parallel.

7. Handpiece according to claim 1,
wherein at least one of
the stop and the counter stop has oblique or rounded lead-in surfaces.

8. Handpiece according to claim 1,
wherein
the push bottom has a hat-like cross-sectional form and the ring waii is constituted by means of the peripheral wall of the push button.

9. Handpiece according to claim 1,
wherein
the insert part is a screw part.

10. Handpiece according to claim 9,
wherein
between the push button and the screw part there is arranged a compression spring.

11. Handpiece according to claim 10,
wherein
the compression spring is shaped hollow cone like.

* * * * *